(12) United States Patent
Kawami et al.

(10) Patent No.: US 7,053,240 B2
(45) Date of Patent: May 30, 2006

(54) PROCESS FOR SYNTHESIZING DISULFIDES

(75) Inventors: Koh Kawami, Hyogo (JP); Osamu Tokuda, Kyoto (JP); Yoshihide Niimoto, Hyougo (JP)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 11/016,441

(22) Filed: Dec. 17, 2004

(65) Prior Publication Data
US 2005/0137419 A1 Jun. 23, 2005

Related U.S. Application Data

(60) Provisional application No. 60/530,162, filed on Dec. 17, 2003.

(51) Int. Cl.
C07F 9/38 (2006.01)
C07C 309/20 (2006.01)
C07C 323/52 (2006.01)

(52) U.S. Cl. .......................... 562/103; 562/22; 562/23; 562/594

(58) Field of Classification Search ................. 562/22, 562/23, 103, 594
See application file for complete search history.

(56) References Cited

U.S. PATENT DOCUMENTS

| 4,220,660 | A |   | 9/1980 | Brock |   |
|---|---|---|---|---|---|
| 5,789,000 | A |   | 8/1998 | Hausheer et al. |   |
| 5,808,140 | A |   | 9/1998 | Haridas |   |
| 5,922,902 | A | * | 7/1999 | Haridas | 562/20 |
| 6,504,049 | B1 |   | 1/2003 | Kochat |   |
| 2004/0024346 | A1 |   | 2/2004 | Miethke |   |

FOREIGN PATENT DOCUMENTS

DE 154815 4/1982
WO WO 02/06216 A1 1/2002

* cited by examiner

Primary Examiner—Peter O'Sullivan
(74) Attorney, Agent, or Firm—Akin Gump Strauss Hauer & Feld, LLP

(57) ABSTRACT

This invention relates to a process for producing a substantially pure disulfide compound of Formula II as disclosed herein, such as disodium 2,2'-dithiobis ethane sulfonate, by an efficient procedure from available, relatively inexpensive raw materials.

16 Claims, No Drawings

PROCESS FOR SYNTHESIZING DISULFIDES

CROSS-REFERENCE TO RELATED APPLICATIONS

This application is entitled to priority pursuant to 35 U.S.C. § 119(e) to U.S. Provisional Patent Application No. 60/530,162, filed Dec. 17, 2003.

BACKGROUND OF THE INVENTION

This invention relates to a chemical synthetic process and will have application to a process for synthesizing disulfide compounds and intermediates thereof.

Mesna (sodium 2-mercaptoethane sulfonate; Mesnex®; Uromitexan®) and dimesna (disodium 2,2'-dithiobis ethane sulfonate; BNP7787; Tavocept™) are known therapeutic compounds that have heretofore demonstrated a wide variety of therapeutic uses. Both mesna and dimesna have been shown to be effective protective agents against certain specific types of toxicity associated with the administration of cytotoxic drugs used to treat patients for various types of cancer.

In particular, mesna is an approved agent in most major markets, and has been used with some success in mitigating the toxic effects of cytotoxic agents such as ifosfamide, oxazaphosphorine, melphalane, cyclophosphamide, trofosfamide, sulfosfamide, chlorambucil, busulfan, triethylene thiophosphamide, triaziquone, and others, as disclosed in U.S. Pat. No. 4,220,660, issued Sep. 2, 1980.

Dimesna is in late stage human clinical trials in most major pharmaceutical markets, and has exhibited efficacy in mitigating the undesired toxic effects of various platinum antineoplastic agents, as well as the neurotoxic effects of paclitaxel.

Further, pharmacological profiles of each compound indicate that, if proper conditions are maintained, mesna and dimesna do not prematurely inactivate primary therapeutic drugs to a significant degree. Thus, neither compound is likely to significantly reduce activity of the chemotherapeutic agent, and in many cases, dimesna has been observed to potentiate the effect of the main drug on targeted cancer cells.

The structures of both mesna and dimesna are shown below:

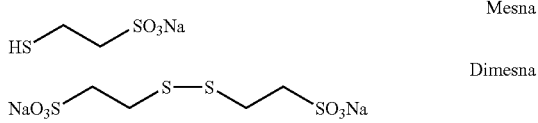

As is well known, dimesna is an oxidative dimer of mesna. In the slightly basic (pH~7.3), oxygen rich environment found in blood plasma, dimesna is present in large part in its oxidized form. In mildly acidic, low oxygen conditions, in the presence of a reducing agent such as glutathione reductase, conditions prevalent in the kidneys, dimesna is reduced to mesna.

Mesna acts as a protective agent for a number of cytotoxic agents by converting a toxic metabolite of the cytotoxic agent (acrolein in the case of ifosfamide) to a relatively harmless compound in vivo. This action is particularly evidenced in the coadministration of mesna and an oxazaphosphorine. Dimesna acts as a protective agent by converting a toxic hydroxy or aquo moiety of the active agent to a relatively harmless mercaptan, particularly in the administration of dimesna along with a platinum agent.

Mesna and dimesna, as well as some analogues of these compounds, have excellent toxicity profiles in mammalian species. Dimesna has been administered intravenously to mice and dogs in doses higher than the accepted oral LD50 for common table salt (3750 mg/kg), with no adverse effects.

Mesna, and other analogues with free thiol moieties, constitute the more physiologically active form of the two types of compounds described in this specification. These compounds manifest their activity by providing free thiol moieties for terminal substitution at locations where a terminal leaving group of appropriate configuration is located.

Dimesna and other disulfides can be activated intracellularly by glutathione reductase, a ubiquitous enzyme, thereby generating high concentrations of intracellular free thiols. These free thiols act to scavenge the free radicals and other nucleophilic compounds often responsible for causing cell damage.

This profile is especially significant in explaining the success of dimesna in controlling and mitigating the toxic effects of platinum complex antitumor drugs. The mechanism for action in the case of cisplatin (cis-diammine dichloro platinum) is explained in U.S. Pat. No. 5,789,000, the disclosure of which is incorporated herein by reference.

Mesna, dimesna, and analogues of these compounds have been the subject of several prior pharmaceutical uses described in the literature and in prior patents, both in the United States and around the world.

Mesna, dimesna, and analogues thereof have been previously synthesized from commonly available starting materials, using acceptable routes well known in the art. See, for example, U.S. Pat. No. 5,808,140. One such method involves the two-step, single pot synthetic process for making dimesna, and other sulfur-containing alkali metal compounds of the following Formula I:

wherein:

$R^1$ is hydrogen, —X-lower alkyl or —X-lower alkyl-$R^3$;

$R^2$ is -lower alkyl-$R^4$;

$R^3$ and $R^4$ are each individually —$SO_3M$ or —$PO_3M_2$;

X is absent or is sulfur; and

M is an alkali metal.

The prior process involves a two-step single pot synthetic process, which results in the conversion of an alkenyl sulfonate salt or acid to the desired Formula I compound. The process in the case of mesna is a single step process that converts the alkenyl sulfonate salt to mesna or a mesna derivative by reacting with an alkali metal sulfide or with hydrogen sulfide.

If the desired end product is dimesna or a dimesna analogue, a two-step single pot process is involved. Step 1 is as described above. Step 2 of the process is performed in the same reaction vessel as Step 1 without the need to purify or isolate the mesna formed during that step. Step 2 includes the introduction of oxygen gas into the vessel, along with an increase in pressure and temperature above ambient values, at least 20 pounds per square inch (psi) and at least 60° C. Dimesna or a derivative thereof is formed in essentially quantitative yield.

Hitherto, it is known that disodium 2,2'-dithiobis ethane sulfonate is produced, for example, by oxidizing sodium 2-mercaptoethane sulfonate, which is obtained by addition to sodium vinyl sulfonate, with oxygen at 60° C. However, this process has a problem, in that it produces a by-product, disodium 2,2'-monothiobis ethane sulfonate, that is difficult to remove.

A method is also known for producing disodium 2,2'-dithiobis ethane sulfonate which comprises allowing sodium 2-bromoethane sulfonate to react with sodium thioacetate, neutralizing the product to give sodium 2-mercaptoethane sulfonate and oxidizing it with oxygen to afford disodium 2,2'-dithiobis ethane sulfonate (U.S. Published Patent Application Publication No. US 2004/0024346 A1, published Feb. 5, 2004). In this method, several unknown by-products are formed at 50–60° C., recommended as the oxidizing temperature, and it is difficult to remove them. Further, solids tend to be produced while drying, because the solvent for crystallizing is a mixture of ethanol with water.

The raw material, sodium 2-bromoethane sulfonate, is known to be prepared by allowing a 1:1.9 mixture of isethionic acid with sodium isethionate to react with hydrobromic acid, cooling the product to give crystals and recrystallizing from 96% ethanol (German Democratic Republic Patent No. DD 154,815). However, isethionic acid is expensive.

Therefore, there is a need for and it is desired to establish a method for producing disodium 2,2'-dithiobis ethane sulfonate from available raw compounds in good yield with high purity. The present invention satisfies this need.

BRIEF SUMMARY OF THE INVENTION

This invention relates to a novel and economical process for synthesis of dimesna or a related disulfide compound of Formula II:

$$R^5\text{—S—S—}R^2; \quad (II)$$

wherein:

$R^5$ is -lower alkyl or -lower alkyl-$R^6$;

$R^2$ is -lower alkyl-$R^4$;

$R^4$ and $R^6$ are each individually —$SO_3M$, —$PO_3M_2$ or —$CO_2M$; and

M is an alkali metal.

This process is carried out in an aqueous solution in one pot or one vessel, and includes an initial step of halogenating a starting material having a Formula III:

$$R^2\text{—Y} \quad (III)$$

wherein:

Y is a displaceable group displaceable by a $S_N2$ nucleophilic substitution reaction; to form a first intermediate having a Formula (IV):

$$R^2\text{-A}; \quad (IV)$$

wherein:

A is a halogen;

which is reacted with an alkali metal mecaptan having a base-sensitive labile protective group to form a second intermediate having a Formula (V):

$$R^2\text{—S-Z}; \quad (V)$$

wherein:

Z is a base-sensitive labile protective group;

which is reacted with a strong base to form a third intermediate having a Formula (VI):

$$R^2\text{—SH}; \quad (VI)$$

which is then oxidized to form the disulfide compound of Formula II, which is then isolated.

An object of this invention is to provide for a novel process for synthesizing reducible disulfides. Preferably, the disulfides, such as dimesna, are pharmaceutically active.

DETAILED DESCRIPTION OF THE INVENTION

The preferred embodiments herein described are not intended to be exhaustive or to limit the invention to the precise form disclosed. They have been chosen and described to explain the principles of the invention, and its application and practical use to thereby enable others skilled in the art to follow and apply its teachings.

Definitions

"About" as used herein means plus or minus ten percent (±10%) of the value to which the term "about" relates.

"Halogen" and related terms such as halogenating, halo, haloacid, as used herein means chlorine, bromine or iodine, but not fluorine, and such related terms refer to these halogens but not fluorine.

"Lower alkyl" as used herein means a straight chain alkyl group of 1 to 4 carbon atoms.

"Percent" or "%" as used herein means percent by weight of the overall composition containing the compound or other component with which percent or % is used, except with reference to the definition of "about" set forth above, where percent or % merely refers to any value to which "about" relates.

"Substantially pure" as used herein means at least 90% pure, preferably at least 95% pure, and more preferably at least 99% pure.

The present invention is a process for making compounds of Formula II:

$$R^5\text{—S—S—}R^2; \quad (II)$$

wherein:

$R^5$ is -lower alkyl or -lower alkyl-$R^6$;

$R^2$ is -lower alkyl-$R^4$;

$R^4$ and $R^6$ are each individually —$SO_3M$, —$PO_3M_2$ or —$CO_2M$; and

M is an alkali metal; and wherein the lower alkyl is preferably ethyl or propyl, and more preferably ethyl; R5 is preferably -lower alkyl-$R^6$; preferably each of $R^4$ and $R^6$ is —$SO_3M$ or —$PO_3M_2$; and more preferably each of $R^4$ and $R^6$ is —$SO_3M$; and M is preferably Na.

This process is a one-pot process carried out in an aqueous solution, and includes the steps set forth above in the Summary, to form a substantially pure disulfide compound of Formula II in good yield, especially for a one-pot process.

More particularly, the process for synthesizing a substantially pure disulfide compound of Formula II comprises the steps of:

(a) Halogenating, and preferably brominating, by reacting, preferably with mixing at a rate of about 15 to about 150 rpm, about 1 to about 10 mol equivalents, preferably about 1 to about 5 mol equivalents of a haloacid, preferably HBr, in aqueous solution with about 1 mol equivalent of a starting material of Formula III:

$$R^2\text{—Y} \quad (III)$$

wherein:

Y is a displaceable group displaceable by a $S_N2$ nucleophilic substitution reaction; and wherein the lower alkyl is preferably ethyl or propyl, and more preferably ethyl; preferably $R^4$ is —$SO_3M$ or —$PO_3M_2$; and more preferably $R^4$ is —$SO_3M$; and M is preferably Na; and the displaceable group may be any suitable displaceable group, such as, without limitation, hydroxyl, mesyl or tosyl, with hydroxyl being preferred. The preferred starting materials include any alkali isethionate salt, such as sodium isethionate or potassium isethionate, and preferably is sodium isethionate. Upon completion of the reaction a first intermediate of Formula IV is obtained and isolated:

$$R^2\text{-A};\qquad\qquad(IV)$$

wherein:

A is a halogen; and wherein the lower alkyl is preferably ethyl or propyl, and more preferably ethyl; preferably $R^4$ is —$SO_3M$ or —$PO_3M_2$; and more preferably $R^4$ is —$SO_3M$; and M is preferably Na; and A is preferably bromine. The presently more preferred first intermediate is 2-bromoethane sulfonate, isolated as crystals.

(b) The first intermediate is washed with water, acetone or a protic solvent, such as, without limitation, aqueous methanol, aqueous ethanol, aqueous 2-propanol or aqueous 2-methyl-1-propanol. For pharmaceutical uses of the Formula II product, acetone or aqueous ethanol is preferred.

(c) The washed first intermediate from step (b) is then reacted in aqueous solution with an alkali metal mecaptan having a base-sensitive labile protective group to form a second intermediate having a Formula (V):

$$R^2\text{—S-Z};\qquad\qquad(V)$$

wherein:

Z is a base-sensitive labile protective group; and wherein the lower alkyl is preferably ethyl or propyl, and more preferably ethyl; preferably $R^4$ is —$SO_3M$ or —$PO_3M_2$; and more preferably $R^4$ is —$SO_3M$; and M is preferably Na; and Z is any suitable base-sensitive labile protective group, such as, without limitation, acetyl, mesyl or tosyl, and preferably acetyl. The presently preferred alkali metal mecaptan with the base-sensitive labile protective group is sodium thioacetate, and the presently preferred second intermediate is sodium 2-acetylthioethane sulfonate. This step preferably includes adding, preferably with mixing at a rate of about 15 to about 150 rpm, the alkali metal mecaptan having a base-sensitive labile protective group to the aqueous solution of the first intermediate from step (b) over a period of about 15 to about 120 minutes while maintaining a temperature of about 15° C. to about 90° C., with agitation for a time such that the level of impurity is less than about 5%.

(d) The second intermediate from step (c) is reacted, preferably with mixing at a rate of about 15 to about 150 rpm, in aqueous solution with about 1 to about 3 mol equivalents, preferably about 1.1 to about 1.4 mol equivalent of a strong base, such as, without limitation, NaOH, KOH, $Na_2CO_3$ or $K_2CO_3$ and adjusting the pH of the solution to a pH of about 6.5 to about 8.0 with an acid, such as, without limitation, acetic acid, oxalic acid or citric acid, preferably acetic acid, or with a base, such as, without limitation, NaOH, KOH, $Na_2CO_3$ or $K_2CO_3$, preferably NaOH, to form a third intermediate having a Formula (VI):

$$R^2\text{—SH};\qquad\qquad(VI)$$

wherein the lower alkyl is preferably ethyl or propyl, and more preferably ethyl; preferably $R^4$ is —$SO_3M$ or —$PO_3M_2$; and more preferably $R^4$ is —$SO_3M$; and M is preferably Na. The presently preferred third intermediate is sodium 2-mercaptoethane sulfonate.

(e) The third intermediate from step (d) is then oxidized in a known manner, such as, without limitation, with oxygen, iodine or silver nitrate, to give an aqueous solution of a compound of Formula II, wherein the lower alkyl is preferably ethyl or propyl, and more preferably ethyl; $R^5$ is preferably -lower alkyl-$R^6$; preferably each of $R^4$ and $R^6$ is —$SO_3M$ or —$PO_3M_2$; and more preferably each of $R^4$ and $R^6$ is —$SO_3M$; and M is preferably Na. This oxidation step presently is preferably conducted using an oxygen-containing gas at elevated pressure. The oxidation step is more preferably conducted using air, oxygen at a purity of about 60% to about 95% or a mixture of oxygen and nitrogen where the oxygen is present at about 50% to about 99%, and most preferably air, where the oxygen or oxygen-containing gas is pressurized to about 0.1 MPa to about 10 MPa, at a temperature of about 20° C. to about 80° C., preferably about 25° C. to about 60° C. The present preferred product of Formula II is dimesna, namely, disodium 2,2'-dithiobis ethane sulfonate.

(f) The aqueous solution of the compound of Formula II, such as disodium 2,2'-dithiobis ethane sulfonate, is then concentrated by distilling away a portion of the aqueous solution and then cooling the aqueous solution to give crystals of the Formula II compound, such as disodium 2,2'-dithiobis ethane sulfonate crystals.

(g) The crystals of the compound of Formula II from step (f), such as disodium 2,2'-dithiobis ethane sulfonate crystals, are then washed in a known manner to provide a substantially pure compound of Formula II, such as disodium 2,2'-dithiobis ethane sulfonate.

This process produces substantially pure compounds of Formula II, such as disodium 2,2'-dithiobis ethane sulfonate, in good yield, such as about 60% by weight to about 80% by weight, which is quite a good yield for a one-pot process, after crystallization. To improve the purity of the final product, the starting materials and all reactants should have a purity of at least about 90%, and preferably at least about 95%. Preferably the disulfide of Formula II produced by this process is pharmaceutically active.

Preferred embodiments will now be described in more detail with reference to the following specific, non-limiting examples.

EXAMPLE 1

Production of Sodium 2-bromoethane Sulfonate

After 1018 g of 47% hydrobromic acid were added dropwise to 292 g of 60% aqueous sodium isethionate solution, the mixture was heated under reflux and 348 g were distilled off at normal pressure.

The residue was cooled to 50° C. and 252 g of 47% hydrobromic acid were added, then further cooled from 50° C. to 5° C. The precipitated crystals were filtered out at about 5° C. and washed with 77.1 g of 47% hydrobromic acid being cooled to about 5° C. and then 17.5 g of water being cooled to about 5° C.

The crystals were washed twice with a mixture of 408.6 g of acetone and 47.4 g of water being cooled to about 5° C., and further washed twice with 221 g of acetone being cooled to about 5 ° C.

The crystals were dried under reduced pressure to afford 120 g of sodium 2-bromoethane sulfonate.

EXAMPLE 2

Production of Disodium 2,2'-dithiobis Ethane Sulfonate

To a mixture of 50.1 g of water with 24.4 g of thioacetic acid, 50.7 g of 25% aqueous sodium hydroxide solution were added dropwise at 10–30° C. This solution was added dropwise to a solution of 63.3 g of sodium 2-bromoethane sulfonate and 70 g of water at 50–70° C. and allowed to react at 80–90° C. for 2 hours.

Thereto 54.2 g of 25% aqueous sodium hydroxide solution were added and allowed to react at refluxing temperature (about 105° C.) until the end of the reaction was confirmed by HPLC. After addition of 3.25 g of acetic acid, the reaction mixture was refluxed for 6 hours and then cooled to about 30° C. The pH of the mixture was adjusted to 7.3 with 25% sodium hydroxide solution. Oxygen was allowed to react with 260 mL of aqueous sodium 2-mercapto ethane sulfonate solution obtained above at about 30° C. and 0.5–0.6 MPa of oxygen pressure.

When the end of the reaction was confirmed by HPLC, the reaction was stopped and the mixture was neutralized with acetic acid. The mixture was heated to about 70° C. and it was observed that the mixture had been dissolved. After that, the mixture was filtered with a filtering assistant agent (radiolite) and the filtering assistant agent was washed with 10 g of water.

The mixture was concentrated under reduced pressure (about 10 kPa) at 70° C. When the amount of the distilled out water became 60 g, the concentration was stopped and it was observed that the mixture remained dissolved at about 75° C. Cooling the mixture, crystallization began at 60±5° C. After aging for about 30 minutes, the mixture was cooled to 25° C. and the crystals were aged for 2 hours at 25° C.

The crystals were filtered out and washed with 24 g of water being cooled to 2° C. and then 48 mL of 70% aqueous ethanol solution. Drying the crystals at about 70° C. afforded 39.1 g of substantially pure disodium 2,2'-dithiobis ethane sulfonate crystals. The yield was 77.6% after crystallization. The purity of the product was 99.4%.

According to the present invention, compounds of Formula II, such as disodium 2,2'-dithiobis ethane sulfonate, can be produced by an efficient procedure from available, relatively less expensive raw compounds in good yield with high purity. The above details are not limitative of the invention, which is defined by the scope of the following claims.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A process of making a disulfide compound of Formula II:

$$R^5—S—S—R^2; \quad (II)$$

wherein:
$R^5$ is -lower alkyl or -lower alkyl-$R^6$;
$R^2$ is -lower alkyl-$R^4$;
$R^4$ and $R^6$ are each individually —$SO_3M$, —$PO_3M_2$ or —$CO_2M$; and
M is an alkali metal;
the process comprising
(a) halogenating a starting material having a Formula III:

$$R^2—Y \quad (III)$$

wherein:
Y is a displaceable group displaceable by a $S_N2$ nucleophilic substitution reaction; to form a first intermediate having a Formula (IV):

$$R^2\text{-}A; \quad (IV)$$

wherein:
A is a halogen;
(b) reacting the first intermediate with an alkali metal mecaptan having a base-sensitive labile protective group to form a second intermediate having a Formula (V):

$$R^2—S—Z; \quad (V)$$

wherein:
Z is a base-sensitive labile protective group;
(c) reacting the second intermediate with a strong base to form a third intermediate having a Formula (VI):

$$R^2—SH; \quad (VI)$$

(d) oxidizing the third intermediate to form the disulfide compound of Formula II; and
(e) isolating the compound of Formula II.

2. The process of claim 1, wherein the lower alkyl is ethyl or propyl; $R^5$ is -lower alkyl-$R^6$; each of $R^4$ and $R^6$ is —$SO_3M$ or —$PO_3M_2$; and M is Na.

3. The process of claim 2, wherein the lower alkyl is ethyl; and each of $R^4$ and $R^6$ is —$SO_3M$.

4. The process of claim 1, wherein the halogen is bromine.

5. The process of claim 1, wherein the oxidizing step (d) is conducted using oxygen-containing gas at elevated pressure.

6. The process of claim 1, wherein the strong base is selected from the group consisting of NaOH, KOH, $Na_2CO_3$ and $K_2CO_3$.

7. The process of claim 6, wherein the strong base is NaOH.

8. A process for synthesizing a substantially pure disulfide compound of Formula II:

$$R^5—S—S—R^2; \quad (II)$$

wherein:
$R^5$ is -lower alkyl or -lower alkyl-$R^6$;
$R^2$ is -lower alkyl-$R^4$;
$R^4$ and $R^6$ are each individually —$SO_3M$, —$PO_3M_2$ or —$CO_2M$; and
M is an alkali metal;
the process comprising the steps of:
(a) reacting with a haloacid in an aqueous solution a starting material having a Formula III:

$$R^2—Y \quad (III)$$

wherein:
Y is a displaceable group displaceable by a $S_N2$ nucleophilic substitution reaction; to form a first intermediate having a Formula (IV):

$$R^2\text{-}A; \quad (IV)$$

wherein:
A is a halogen;
(b) reacting in the aqueous solution the first intermediate with an alkali metal mecaptan having a base-sensitive labile protective group to form a second intermediate having a Formula (V):

$$R^2—S—Z; \quad (V)$$

wherein:
Z is a base-sensitive labile protective group;
(c) washing the second intermediate with a solvent selected from the group consisting of water, acetone and a protic solvent;

(d) reacting the washed second intermediate with a strong base and then adjusting the pH with acid or base to a pH of about 6.5 to about 8.0 to form a third intermediate having a Formula (VI):

$$R^2\text{—SH;} \tag{VI}$$

(e) oxidizing the third intermediate to form an aqueous solution of the compound of Formula II;

(f) concentrating the aqueous solution of the compound of Formula II by distilling away a portion of the aqueous solution and then cooling the aqueous solution to give crystals of the Formula II compound; and (g) washing the crystals of the compound of Formula II to provide a substantially pure compound of Formula II.

9. The process of claim 8, wherein the lower alkyl is ethyl or propyl; $R^5$ is -lower alkyl-$R^6$; each of $R^4$ and $R^6$ is —SO$_3$M or —PO$_3$M$_2$; and M is Na.

10. The process of claim 9, wherein the lower alkyl is ethyl; and each of $R^4$ and $R^6$ is —SO$_3$M.

11. The process of claim 8, wherein the haloacid is HBr and the halogen is bromine.

12. The process of claim 8, wherein the oxidizing step (e) is conducted using oxygen-containing gas at elevated pressure.

13. The process of claim 8, wherein the strong base is selected from the group consisting of NaOH, KOH, Na$_2$CO$_3$ and K$_2$CO$_3$.

14. The process of claim 13, wherein the strong base is NaOH.

15. A process for synthesizing a substantially pure disulfide, the process comprising the steps of:

(a) reacting in aqueous solution sodium isethionate with hydrobromic acid to obtain and isolate sodium 2-bromoethane sulfonate crystals;

(b) washing the sodium 2-bromoethane sulfonate crystals;

(c) reacting in the aqueous solution the sodium 2-bromoethane sulfonate with sodium thioacetate to obtain sodium 2-acetylthioethane sulfonate;

(d) reacting in aqueous solution the sodium 2-acetylthioethane sulfonate with a strong base, adding acetic acid and then adjusting the pH of the solution to a pH of about 6.5 to about 8.0 to give an aqueous solution of sodium 2-mercaptoethane sulfonate;

(e) oxidizing the sodium 2-mercaptoethane sulfonate to give an aqueous solution of disodium 2,2'-dithiobis ethane sulfonate;

(f) distilling away a portion of the aqueous solution of disodium 2,2'-dithiobis ethane sulfonate and then cooling the aqueous solution to give disodium 2,2'-dithiobis ethane sulfonate crystals; and (g) washing the disodium 2,2'-dithiobis ethane sulfonate crystals.

16. The process of claim 15 wherein the strong base is NaOH.

* * * * *